United States Patent [19]

Haugwitz et al.

[11] 4,293,569
[45] Oct. 6, 1981

[54] SUBSTITUTED PHENYLGUANINDINES AND METHOD

[75] Inventors: Rudiger D. Haugwitz, Titusville; Peter C. Wade, Pennington; Barbara V. Maurer, Titusville, all of N.J.

[73] Assignee: E. R. Squibb & Sons, Inc., Princeton, N.J.

[21] Appl. No.: 905,265

[22] Filed: May 12, 1978

[51] Int. Cl.$^3$ .............. C07C 155/02; C07C 149/437; C07C 147/14; A61K 31/325
[52] U.S. Cl. .................. 424/300; 260/397.6; 260/455 A; 560/9; 560/13
[58] Field of Search ............. 560/13, 9; 260/455 A, 260/397.6; 424/300

[56] References Cited

U.S. PATENT DOCUMENTS

| | | | |
|---|---|---|---|
| 3,828,094 | 8/1974 | Widdig | 560/13 |
| 3,993,682 | 11/1976 | Kollig | 560/9 |
| 4,024,176 | 5/1977 | Kollig | 560/9 |
| 4,032,655 | 6/1977 | Kollig | 424/300 |
| 4,246,260 | 1/1981 | Kolling | 560/13 |

OTHER PUBLICATIONS

Lowy, "Introduction to Organic Chemistry," 7th Ed., p. 215 (1951).

Primary Examiner—Natalie Trousof
Assistant Examiner—Michael Shippen
Attorney, Agent, or Firm—Lawrence S. Levinson; Burton Rodney

[57] ABSTRACT

Phenylguanidine derivatives are provided having the structure

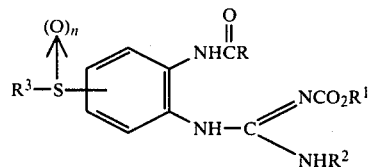

wherein R is hydrogen, lower alkyl, cycloalkyl, lower alkoxy, phenyl, phenylalkyl, phenoxy, phenylalkoxy, lower alkoxyalkyl, phenoxyalkyl, alkylamino, dialkylaminoalkyl, alkylthio, phenylthio, phenylthioalkyl, and alkylthioalkyl; $R^1$ is lower alkyl or benzyl; $R^2$ is hydrogen, lower alkoxy carbonyl, and lower alkanoyl; $R^3$ is lower alkyl, cycloalkylalkyl, lower alkenyl, lower alkynyl or benzyl; and n is 0 or 1. These compounds are useful as anthelmintic agents.

9 Claims, No Drawings

SUBSTITUTED PHENYLGUANINDINES AND METHOD

DESCRIPTION OF THE INVENTION

The present invention relates to phenylguanidine derivatives which are useful as anthelmintic agents and have the structure

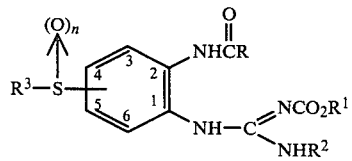

wherein R is hydrogen, lower alkyl, cycloalkyl, lower alkoxy, phenyl, phenylalkyl, phenoxy, phenylalkoxy, lower alkoxyalkyl, phenoxyalkyl, alkylamino, dialkylaminoalkyl, alkylthio, phenylthio, phenylthioalkyl and alkylthioalkyl; $R^1$ is lower alkyl or benzyl; $R^2$ is hydrogen, lower alkoxycarbonyl, and lower alkanoyl; $R^3$ is lower alkyl, cycloalkylalkyl, lower alkenyl, lower alkynyl or benzyl; and n is 0 or 1.

The term "lower alkyl" or "alkyl" as used herein whether employed as an independent substituent or as a part of another substituent includes straight or branched chain aliphatic hydrocarbon radicals having up to and including 7 carbon atoms, preferably 1 to 3 carbons, such as methyl, ethyl, propyl, isopropyl, butyl, isobutyl, t-butyl, amyl, hexyl, heptyl and the like.

The term "lower alkoxy" or "alkoxy" whether employed as an independent substituent or as a part of another substituent includes any of the above lower alkyl or alkyl groups linked to an oxygen atom.

The term "phenylalkyl" as used herein refers to lower alkyl groups as discussed above having a phenyl substituent, such as benzyl.

The term "cycloalkyl" includes cyclic hydrocarbon groups containing 3 to 12 carbons, which include cyclopropyl, cyclobutyl, cyclopentyl, cyclohexyl, cycloheptyl, cyclooctyl, cyclodecyl and cyclododecyl, any of which groups may be substituted with 1, 2, 3 or 4 halogen and/or 1, 2, 3, or 4 lower alkyl groups.

The term "lower alkenyl" refers to an unsaturated hydrocarbon group having from 3 to 6 carbon atoms and a single carbon-carbon double bond. Typical alkenyl groups include, for example, 2-propenyl, 1-propenyl, 1-butenyl, 2-butenyl, 3-butenyl, and the like.

The term "lower alkanoyl" as employed herein refers to any of the above lower alkyl or alkyl groups linked to a carbonyl group.

The term "lower alkynyl" refers to an unsaturated hydrocarbon group having from 3 to 6 carbon atoms, and a single carbon-carbon triple bond. Typical alkynyl groups include, for example, 1-propynyl, 1-butynyl, 2-propynyl, 2-butynyl, 3-butynyl, and the like.

Preferred are those compounds wherein R is lower alkyl, $R^1$ is lower alkyl, $R^2$ is hydrogen or lower alkoxy carbonyl, $R^3$ is lower alkyl and n is 0 or 1.

Thus, the compounds of the invention include the following:

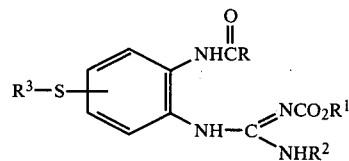

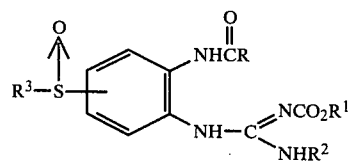

The compounds of structure I may be prepared by reacting anilines of the structure IV

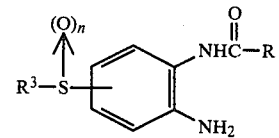

with an S-methylisothiourea V

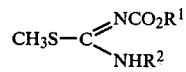

optionally, in the presence of an acid such as p-toluenesulfonic acid or acetic acid. The above reaction is preferably carried out at temperatures ranging from about 50° to about 100° C. for periods ranging from about 1 to about 5 hours.

Compounds of formula I wherein $R^2$ is hydrogen may be prepared by controlled hydrolysis of compounds of the structure

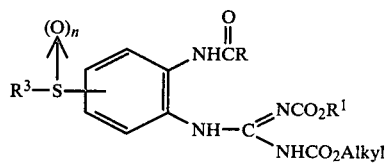

The aniline of structure IV may be prepared by reduction of the nitro derivatives VI

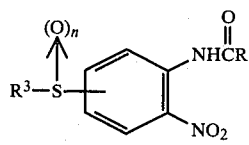

The reduction may be carried out catalytically with hydrogen and platinum or chemically with dithionite, or zinc and acetic acid.

The formula VI nitro derivatives are synthesized by reacting compounds of the structure VII

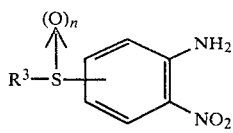

with an appropriate reagent depending upon the type of R group to be present in the formula VI compound.

Thus, for example, where R is hydrogen, the formula VII compound is reacted with formic acid to form VI.

Where R is lower alkyl, cycloalkyl, phenyl, phenylalkyl, alkylthioalkyl, alkoxyalkyl, phenoxyalkyl, phenylthioalkyl or dialkylaminoalkyl, the formula VII compound is reacted with the requisite carboxylic acid chloride or anhydride to form VI.

Where R is lower alkoxy, phenoxy, phenylthio or benzyloxy, the formula VII compound is reacted with the requisite haloformate ester to form VI.

Where R is lower alkylamino, the formula VII compound is reacted with the requisite isocyanate to form VII.

Compounds of the structure VII are prepared by reacting VIII

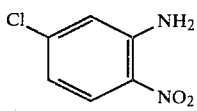

with the appropriate thiol IX or preferably, the thiol salt to furnish VII

The compounds of formula I wherein n is 1 may be prepared by oxidizing compounds of formula I wherein n is 0, that is, compounds of formula II, utilizing one equivalent of an oxidizing agent such as m-chloroperbenzoic acid, sodium m-periodate or hydrogen peroxide in acetic acid. Addition routes are outlined in Houben-Weyl's *Methoden Der Organischen Chemie*, Vol. 9, pp. 211–217 (1955), C. Thieme Verlag, Stuttgart.

The oxidation step may also be introduced at an earlier stage in the reaction sequence. For example, nitro derivative VI where n is 0, or nitro derivative VII where n=0 may be oxidized with any of the aforementioned oxidizing agents to give VI or VII wherein n is 1.

Other starting materials employed in the above reactions are either known in the art or easily prepared according to conventional techniques.

In certain instances, the compounds of formula I form physiologically acceptable acid-addition salts with inorganic and organic acids. These salts frequently provide useful means for isolating the products from reaction mixtures by forming the salt in a medium in which it is insoluble. The free base may then be obtained by neutralization. Then any other salt may again be formed from the free base and the appropriate inorganic acid. Illustrative are the hydrohalides, especially the hydrochloride and hydrobromide which are preferred, sulfate, nitrate, tartrate, methanesulfonate, benzenesulfonate, toluenesulfonate, and the like.

The compounds of formula I have anthelmintic activity and are useful in the treatment and/or prevention of helminthiasis, a parasitic disease which causes widespread and often serious infection in domesticated animals such as swine, horses, cattle, dogs, cats and sheep.

The compounds are useful in treating infections caused by Haemonchus, Ostertagia, Trichostrongylus, Cooperia, Dictyocaulus, Nematodirus, Bunostomum, Strongyloides, Oesophagostomum, Trichuris, Moniezia, and liver flukes (for example in sheep). In treating domesticated animals, the compounds are given orally; however, other routes such as parenterally, for example, subcutaneously, intravenously, interperitoneally and intramuscularly may be employed.

Where the compounds are administered orally, they may be mixed with a nontoxic, edible carrier to form a feed supplement, or may be administered in unit dosage forms such as powders, capsule, tablet, boluses, drenches, etc.

Where the compounds are administered parenterally, they may be dispersed (for example, suspended) in nontoxic non-pyrogenic physiologically acceptable carriers such as water, benzyl benzoate, 1,3-butylene glycol, ethyl oleate, glyceryl triacetate, castor oil, sesame oil, and sesame oil:benzyl benzoate (1:1). The parenteral product will usually take the form of a suspension containing from about 1 to about 10% by weight of the compound of formula I in anyone or mixture of the above carriers.

In general, the compounds of formula I exhibit anthelmintic activity when administered to animals (parenterally or orally) in a single dose of about 1 to about 100 mg per kilogram of animal body weight. It is preferred to employ in the range of 2.5–25 mg per kilogram of body weight. The compounds may be divided into a plurality of smaller doses given parenterally or orally over one or more days.

When the compounds of formula I are to be administered in unit dosage form, capsules, boluses or drenches containing the desired amount of anthelmintic distributed in a pharmaceutically acceptable vehicle are usually employed. These are prepared by intimately and uniformly mixing the active ingredient with suitable finely divided diluents, suspending agents, fillers, disintegrating agents and/or binders such as starch, lactose, talc, magnesium stearate, vegetable gums and the like and are compounded by techniques generally known in the art.

The compounds of formula I may also be administered as a component of the feed of the animals or suspended in the drinking water. Thus, novel feed and feed supplement compositions may be prepared in which the compounds of this invention are present as an active anthelmintic ingredient. A typical feed supplement comprises the anthelmintic agent intimately dispersed in or admixed with an inert carrier or diluent, i.e., one that is nonreactive with respect to the anthelmintic agent and that may be administered with safety to the animals. The carrier or diluent is preferably one that is or may be an ingredient of an animal ration. This composition may be mixed with the feed to give any useful desired concentration, preferably about 0.1–2%. Lastly, feeds containing the active ingredient may be made directly by mixing said active ingredient in a feed which is inert to said anthelmintic compounds so as to give feeds having concentrations of anthelmintic agent of from 0.1–2%.

The following examples are provided for illustrative purposes and may include particular features of the invention, however the examples should not be construed as limiting the invention, many variations of which are possible without departing from the spirit of scope thereof. All temperatures are in degrees centigrade.

EXAMPLE 1

[[[2-(Acetylamino)-4-[(2-methylpropyl)thio]phenyl]amino][(methoxycarbonyl)amino]methylene]carbamic acid, methyl ester A. N-[5-[(2-Methylpropyl)thio]-2-nitrophenyl]acetamide A mixture of 11.3 g (0.05 mole) of 4-[(2-methylpropyl)thio]-2-nitroaniline and 10 ml of acetyl chloride is heated gently on the steam bath (approximately 15 seconds) until the reaction is initiated. After stirring at room temperature for 1 hour, the reaction-mixture is exhaustively extracted with boiling petroleum ether (b.p. 30°-60°). The petroleum ether fractions are combined and reduced in volume. Upon cooling the amide crystallizes in yellow needles to give 11.1 g, m.p. 53°-55° C.

B. N-[2-Amino-5[(2-methylpropyl)thio]phenyl]acetamide

A mixture of 10.72 g (0.04 moles) of the above amide, 1.1 g of $PtO_2$ and 200 ml of absolute ethanol is reduced on the Parr hydrogenator at 50 psi until the theoretical amount of hydrogen is absorbed. The mixture is filtered and evaporated in vacuo. The resulting oil is used in part D.

C. [[(Methoxycarbonyl)amino](methylthio)methylene]carbamic acid, methyl ester

To a solution of 112 g of S-methyl-2-thiourea sulfate in 200 ml of water at 0° C. there is added concurrently 260 ml of 25% NaOH and 160 ml of methyl chloroformate at such a rate that the pH remains between 7 and 8 as monitored by a pH meter. After the addition is complete the mixture is stirred for an additional 2 hours at room temperature. Then 400 ml of water is added and the mixture is extracted with dichloromethane. The organic layers are combined, dried over magnesium sulfate, and evaporated in vacuo to give a white solid. Crystallization from methanol yields 60.4 g, m.p. 99°-101° C.

D. [[[2-(Acetylamino)-4-[(2-methylpropyl)thio]phenyl]amino][(methoxycarbonyl)amino]methylene]carbamic acid, methyl ester To a solution of the above amine from part B in 200 ml of methanol there is added 8.24 g (0.04 moles) of [[(methoxycarbonyl)amino](methylthio)methylene]carbamic acid, methyl ester (prepared as described in Part C) and 1.0 g of p-toluenesulfonic acid and the mixture is refluxed for 3 hours. The reaction mixture is filtered hot, reduced in volume and cooled. The resulting solid is filtered off and crystallized from absolute ethanol to yield 8.6 g of product, m.p. 136°-138° C. dec.

EXAMPLE 2

[[[2-(Acetylamino)-4-[(2-methylpropyl)sulfinyl]phenyl]amino][(methoxycarbonyl)amino]methylene]carbamic acid, methyl ester To a solution of 3.9 g (0.01 mole) of [[[2-(acetylamino)-4-[(2-methylpropyl)thio]phenyl]amino][-(methoxycarbonyl)amino]methylene carbamic acid, methyl ester in 250 ml of chloroform there is added 2.0 g (0.01 mole of 85% m-chloroperoxybenzoic acid in 10 ml of chloroform with ice bath cooling. The reaction mixture is allowed to warm to room temperature and then stirred for 3 hours. The reaction mixture is washed with aqueous potassium carbonate and then with water until the pH is 7. The organic layer is dried ($MgSO_4$), filtered, and evaporated in vacuo. The residue is crystallized from ethanol to yield 1.8 g, m.p. 178°-180° C. dec.

EXAMPLE 3

[[[2-(Acetylamino)-5-[(2-methylpropyl)thio]phenyl]amino]aminomethylene]carbamic acid, methyl ester To a solution of 3.9 g of the product of Example 1, in 50 ml of methanol at 50° C., there is added a solution of 0.4 g of sodium hydroxide in 30 ml of methanol. After stirring for 5 minutes the mixture is cooled and the solvent is removed in vacuo. The residue is crystallized from chloroform to yield 2.1 g of the title compound, m.p. 180°-183.5° C.

EXAMPLES 4 TO 19

Following the procedure of Example 1 but substituting for 4-[(2-methylpropyl)thio]-2-nitroaniline, the aniline derivative shown in Column I of Table I set out below, substituting for acetyl chloride, the compound shown in Column II, and substituting for [[(methoxycarbonyl)amino](methylthio)methylene]carbamic acid, methyl ester, the compound shown in Column III, the product in accordance with the present invention shown in Column IV is obtained.

TABLE I

| | Column I | Column II | Column III | Column IV | | | |
|---|---|---|---|---|---|---|---|
| Ex. No. | $R^3$ (position of $R^3$—S) | R | $R^1$ | $R^2$ | $R^3$ (position of $R^3$—S) | R | $R^1$ $R^2$ |
| | | | | | as in Column I | as in Column II | as in Column III |
| 4. | i-$C_3H_7$ (5) | $C_2H_5$ | $CH_3$ | $CO_2CH_3$ | (4) | | |
| 5. | ▷—$CH_2$ (5) | $C_6H_5$ | $CH_3$ | $\overset{O}{\underset{\|}{C}}CH_3$ | (4) | | |
| 6. | $CH_2$=CH—$CH_2$ (5) | $CH_2OCH_3$ | $CH_3$ | H | (4) | | |
| 7. | $(CH_3)_2CHCH$ (5) | $CH_2SCH_3$ | $CH_2C_6H_5$ | $\overset{O}{\underset{\|}{C}}CH_2C_6H_5$ | (4) | | |

TABLE I-continued

| Ex. No. | Column I $R^3$ (position of $R^3$—S) | Column II R | Column III $R^1$ | $R^2$ | Column IV $R^3$ | (position of $R^3$—S) | R | $R^1$ | $R^2$ |
|---|---|---|---|---|---|---|---|---|---|
| 8. | CH≡C—CH$_2$—(4) | ▢ | CH$_3$ | COCH$_3$ | | (5) | | | |
| 9. | Cl$_2$C(cyclopropyl)—CH$_2$—(5) | CH$_2$C$_6$H$_5$ | CH$_3$ | H | | (4) | | | |
| 10. | ▢—CH$_2$—(5) | CH$_3$ | C$_2$H$_5$ | CO$_2$C$_2$H$_5$ | | (4) | | | |
| 11. | C$_6$H$_5$CH$_2$ (4) | C$_6$H$_5$ | CH$_3$ | H | | (5) | | | |
| 12. | Cl$_2$,CH$_3$-cyclopropyl—CH$_2$—(5) | CH$_2$SC$_2$H$_5$ | CH$_3$ | H | | (4) | | | |
| 13. | (CH$_3$)$_2$CH—(5) | (CH$_2$)$_2$OCH$_3$ | C$_2$H$_5$ | CO$_2$C$_2$H$_5$ | | (4) | | | |
| 14. | (CH$_3$)$_2$CHCH$_2$—(5) | CH$_3$S—CH$_2$— | CH$_3$ | CO$_2$CH$_3$ | | (4) | | | |
| 15. | △—CH$_2$ (5) | C$_6$H$_5$OCH$_2$— | C$_2$H$_5$ | CO$_2$C$_2$H$_5$ | | (4) | | | |
| 16. | CH$_2$=CHCH$_2$ (5) | C$_6$H$_5$SCH$_2$— | CH$_3$ | CO$_2$CH$_3$ | | (4) | | | |
| 17. | ▢—CH$_2$ (5) | (CH$_3$)$_2$N—CH$_2$— | CH$_3$ | COCH$_3$ | | (4) | | | |
| 18. | Cl$_2$C(cyclopropyl)—CH$_2$—(5) | C$_6$H$_5$CH$_2$ | CH$_3$ | H | | (4) | | | |
| 19. | CH$_2$=CH—CH$_2$ (5) | CH$_3$ | CH$_3$ | H | | (4) | | | |

EXAMPLES 20 TO 29

Following the procedure of Example 1 but substituting for 4-[(2-methylpropyl)thio]-2-nitroaniline, the aniline derivative shown in Column I of Table II set out below, substituting for acetyl chloride, the compound shown in Column II, and substituting for [[(methoxycarbonyl)amino](methylthio)methylene]carbamic acid, methyl ester, the compound shown in Column III, the product in accordance with the present invention shown in Column IV is obtained.

TABLE II

| Ex. No. | Column I $R^3$ (position of $R^3$—S) | Column II R (XCOR, X=Cl, Br) | Column III $R^1$ | $R^2$ | Column IV $R^3$ | (position of $R^3$—S) | R | $R^1$ | $R^2$ |
|---|---|---|---|---|---|---|---|---|---|
| | | | | | as in Column I | | as in Column II | as in Column III | |
| 20. | i-C$_3$H$_7$ (5) | CH$_3$O | CH$_3$ | CO$_2$CH$_3$ | | (4) | | | |
| 21. | ▷—CH$_2$ (5) | C$_2$H$_5$O | C$_2$H$_5$ | C(O)C$_2$H$_5$ | | (4) | | | |
| 22. | CH$_2$=CH—CH$_2$ (5) | OCH$_2$C$_6$H$_5$ | CH$_3$ | H | | (4) | | | |
| 23. | (CH$_3$)$_2$CHCH$_2$(5) | C$_6$H$_5$O | CH$_2$C$_6$H$_5$ | C(O)CH$_2$C$_6$H$_5$ | | (4) | | | |
| 24 | CH≡C—CH$_2$— (4) | (CH$_3$)$_2$CHO | CH$_3$ | COCH$_3$ | | (5) | | | |
| 25 | Cl$_2$C(cyclopropyl)—CH$_2$—(5) | (CH$_3$)$_2$CH—CH$_2$O | CH$_3$ | H | | (4) | | | |
| 26. | ▢—CH$_2$—(5) | OCH$_2$C$_6$H$_5$ | C$_2$H$_5$ | CO$_2$C$_2$H$_5$ | | (4) | | | |
| 27. | C$_6$H$_5$CH$_2$ (4) | C$_6$H$_5$O | CH$_3$ | H | | (5) | | | |

TABLE II-continued

| | Column I | Column II | Column III | Column IV | | | |
|---|---|---|---|---|---|---|---|
| | $R^3-S-\underset{5\ 4\ 3}{\underset{|}{\bigcirc}}\underset{2}{\overset{6\ 1}{\text{—}}}\overset{NH_2}{\underset{NO_2}{}}$ | XCOR<br>X = Cl, Br | $CH_3S-C\overset{NCO_2R^1}{\underset{NHR^2}{\diagdown}}$ | $R^3-S-\underset{5\ 4\ 3}{\underset{|}{\bigcirc}}\underset{2}{\overset{6\ 1}{\text{—}}}\overset{\overset{O}{\overset{||}{NHCR}}}{\underset{NH-C\overset{NCO_2R^1}{\diagdown NHR^2}}{}}$ | | | |
| Ex. No. | $R^3$ (position of $R^3$—S) | R | $R^1$ | $R^2$ | $R^3$ (position of $R^3$—S) | R | $R^1$ $R^2$ |
| 28. | Cl, Cl ⟩<—CH₂— (5)<br>  CH₃ | CH₃O | CH₃ | H | (4) | { as in Column I } | { as in Column III } |
| 29. | (CH₃)₂CH— (5) | C₆H₅S | C₂H₅ | CO₂C₂H₅ | (4) | | |

EXAMPLES 30 TO 39

Following the procedure of Example 1, but substituting for 4-[(2-methylpropyl)thio]-2-nitroaniline, the aniline derivative shown in Column I of Table III set out below, substituting for acetyl chloride, the compound shown in Column II, and substituting for [[(methoxycarbonyl)amino](methylthio)methylene]carbamic acid, methyl ester, the compound shown in Column III, the product in accordance with the present invention shown in Column IV is obtained.

EXAMPLES 40 TO 49

Following the procedure of Example 1 but substituting for 4-[(2-methylpropyl)thio]-2-nitroaniline, the aniline derivative shown in Column I of Table III set out below, substituting for acetyl chloride, formic acid as shown in Column II, and substituting for [[(methoxycarbonyl)amino](methylthio)methylene]carbamic acid, methyl ester, the compound shown in Column III, the product in accordance with the present invention shown in Column IV is obtained.

TABLE III

| | Column I | Column II | Column III | Column IV | | | |
|---|---|---|---|---|---|---|---|
| | $R^3-S-\underset{5\ 4\ 3}{\underset{|}{\bigcirc}}\underset{2}{\overset{6\ 1}{\text{—}}}\overset{NH_2}{\underset{NO_2}{}}$ | RNCO | $CH_3S-C\overset{NCO_2R^1}{\underset{NHR^2}{\diagdown}}$ | $R^3-S-\underset{5\ 4\ 3}{\underset{|}{\bigcirc}}\underset{2}{\overset{6\ 1}{\text{—}}}\overset{\overset{O}{\overset{||}{NHCR}}}{\underset{NH-C\overset{NCO_2R^1}{\diagdown NHR^2}}{}}$ | | | |
| Ex. No. | $R^3$ (position of $R^3$—S) | R | $R^1$ | $R^2$ | (position of $R^3$—S) { as in Column I } | R | $R^1$ $R^2$ { as in Column III } |
| 30. | i-C₃H₇ (5) | CH₃ | CH₃ | CO₂CH₃ | (4) | CH₃NH | |
| 31. | ▷—CH₂— (5) | C₂H₅ | CH₃ | $\overset{O}{\overset{||}{CCH_3}}$ | (4) | C₂H₅NH | |
| 32. | CH₂=CH—CH₂ (5) | (CH₃)₂CH | CH₃ | H | (4) | (CH₃)₂CHNH | |
| 33. | (CH₃)₂CHCH₂ (5) | C₃H₇ | CH₂C₆H₅ | $\overset{O}{\overset{||}{CCH_2C_6H_5}}$ | (4) | C₃H₇NH | |
| 34. | CH≡C—CH₂— (4) | CH₃ | CH₃ | COCH₃ | (5) | CH₃NH | |
| 35. | Cl, Cl ⟩<—CH₂— (5) | C₂H₅ | CH₃ | H | (4) | C₂H₅NH | |
| 36. | ☐—CH₂ (5) | (CH₃)₂CH | C₂H₅ | CO₂C₂H₅ | (4) | (CH₃)₂CHNH | |
| 37. | C₆H₅CH₂ | C₃H₇ | CH₃ | H | (5) | C₃H₇NH | |
| 38. | Cl, Cl ⟩<—CH₂— (5)<br>   CH₃ | CH₃ | CH₃ | H | (4) | CH₃NH | |
| 39. | (CH₃)₂CH— (5) | C₂H₅ | C₂H₅ | CO₂C₂H₅ | (4) | C₂H₅NH | |

TABLE IV

| | Column I | Column II | Column III | Column IV | | | | |
|---|---|---|---|---|---|---|---|---|
| | $R^3-S-$ phenyl with $NH_2$ (position 2) and $NO_2$ (position 1), numbering 3,4,5,6 | HCOOR | $CH_3S-C(=NCO_2R^1)(NHR^2)$ | $R^3-S-$ phenyl with $NHC(=O)R$ and $NH-C(=NCO_2R^1)(NHR^2)$ | | | | |
| Ex. No. | $R^3$ (position of $R^3-S$) | R | $R^1$ | $R^2$ | $R^3$ | (position of $R^3-S$) | R | $R^{11}$ | $R^2$ |
| 40. | i-$C_3H_7$ (4) | H | $CH_3$ | $CO_2CH_3$ | as in Column I | (5) | as in Column II | | as in Column III |
| 41. | cyclopropyl-$CH_2-$(5) | H | $CH_3$ | $COCH_3$ | | (4) | | | |
| 42. | $CH_2=CH-CH_2-$(5) | H | $CH_3$ | H | | (4) | | | |
| 43. | $(CH_3)_2CHCH_2-$(5) | H | $CH_2C_6H_5$ | $CCH_2C_6H_5$ (=O) | | (4) | | | |
| 44. | $CH\equiv C-CH_2-$(4) | H | $CH_3$ | $COCH_3$ | | (5) | | | |
| 45. | Cl,Cl-cyclopropyl-$CH_2-$(5) | H | $CH_3$ | H | | (4) | | | |
| 46. | cyclobutyl-$CH_2-$(5) | H | $CH_3$ | $CO_2CH_3$ | | (4) | | | |
| 47. | $C_6H_5CH_2$ (4) | H | $CH_3$ | H | | (5) | | | |
| 48. | Cl,Cl,$CH_3$-cyclopropyl-$CH_2-$(5) | H | $CH_3$ | H | | (4) | | | |
| 49. | $(CH_3)_2CH-$(5) | H | $CH_3$ | $CO_2CH_3$ | | (4) | | | |

EXAMPLES 50 TO 64

Following the procedure of Example 3, but substituting for [[[2-(acetylamino)-4-[(2-methoxypropyl)thio]-phenyl]amino][(methoxycarbonyl)amino]methylene]-carbamic acid, methyl ester, any of the compounds of Examples 4, 10, 13, 14, 15, 16, 20, 26, 29, 30, 36, 39, 40, 46 and 49, as set out in Column I of Table V below, the corresponding hydrolyzed product shown in Column II is obtained.

TABLE V

| | Column I | | | | Column II | | | |
|---|---|---|---|---|---|---|---|---|
| | $R^3-S-$ phenyl with $NHC(=O)-R$ and $NH-C(=NCO_2R^1)(NHR^2)$ | | | | $R^3-S-$ phenyl with $NHCR(=O)$ and $NH-C(=NCO_2R^1)(NH_2)$ | | | |
| Ex. No. | $R^3$ ($R^3-S$ position) | R | $R^1$ | $R^2$ | ($R^3-S$ position) | $R^3$ | R | $R^1$ |
| 50. | i-$C_3H_7$ (5) | $C_2H_5$ | $CH_3$ | $CO_2CH_3$ | as in Column I | | | |
| 51. | cyclobutyl-$CH_2-$(5) | $CH_3$ | $C_2H_5$ | $CO_2C_2H_5$ | | | | |
| 52. | $(CH_3)_2CH-$(5) | $(CH_2)_2OCH_3$ | $C_2H_5$ | $CO_2C_2H_5$ | | | | |
| 53. | $(CH_3)_2CH_2CH_2$ (5) | $CH_3S-CH_2$ | $CH_3$ | $CO_2CH_3$ | | | | |
| 54. | cyclopropyl-$CH_2$ (5) | $C_6H_5OCH_2$ | $C_2H_5$ | $CO_2C_2H_5$ | | | | |
| 55. | $CH_2=CHCH_2$ (5) | $C_6H_5SCH_2$ | $CH_3$ | $CO_2CH_3$ | | | | |
| 56. | i-$C_3H_7$ (5) | $CH_3O$ | $CH_3$ | $CO_2CH_3$ | | | | |
| 57. | cyclobutyl-$CH_2-$(5) | $OCH_2C_6H_5$ | $C_2H_5$ | $CO_2C_2H_5$ | | | | |
| 58. | $(CH_3)_2CH$ (5) | $C_6H_5S$ | $C_2H_5$ | $CO_2C_2H_5$ | | | | |
| 59. | i-$C_3H_7$(5) | $CH_3NH$ | $CH_3$ | $CO_2CH_3$ | | | | |
| 60. | cyclobutyl-$CH_2-$(5) | $(CH_3)_2CHNH$ | $C_2H_5$ | $CO_2C_2H_5$ | | | | |
| 61. | $(CH_3)_2CH$ (5) | $C_2H_5NH$ | $C_2H_5$ | $CO_2C_2H_5$ | | | | |
| 62. | i-$C_3H_7$(4) | H | $CH_3$ | $CO_2CH_3$ | | | | |
| 63. | cyclobutyl-$CH_2$ (5) | H | $CH_3$ | $CO_2CH_3$ | | | | |
| 64. | $(CH_3)_2CH$ (5) | H | $CH_3$ | $CO_2CH_3$ | | | | |

EXAMPLES 65 TO 126

Following the procedure of Example 2 except substituting the compounds of Examples 3 to 64 for the [[[2-(acetylamino)-4-[(2-methylpropyl)thio]phenyl]amino][-(methoxycarbonyl)amino]methylene]carbamic acid, methyl ester, the corresponding sulfoxides of the compounds of Examples 3 to 64 are obtained.

What is claimed is:

1. A compound of the structure

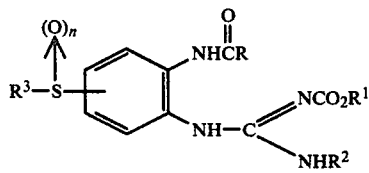

wherein R is hydrogen, lower alkyl, cycloalkyl, lower alkoxy, phenyl, phenylalkyl, lower alkoxyalkyl, phenoxy, phenylalkoxy, phenoxyalkyl, dialkylaminoalkyl, alkylthio, phenylthio, phenylthioalkyl, alkylthioalkyl or cycloalkyl substituted with 1, 2, 3 or 4 halogen groups and/or 1, 2, 3 or 4 lower alkyl groups; $R^1$ is lower alkyl or benzyl, $R^2$ is hydrogen lower alkoxy carbonyl, or lower alkanoyl; $R^3$ is cycloalkylalkyl, benzyl or cycloalkylalkyl wherein the cycloalkyl portion is substituted with 1, 2, 3 or 4 halogen groups and/or 1, 2, 3 or 4 lower alkyl groups; and n is 0 or 1, or a physiologically acceptable salt thereof.

2. The compound as defined in claim 1 wherein n is 0.

3. The compound as defined in claim 1 wherein n is 1.

4. The compound as defined in claim 1 wherein R is lower alkyl, $R^1$ is lower alkyl, $R^2$ is lower alkoxycarbonyl or hydrogen, and n is 0 or 1.

5. The compound as defined in claim 1 wherein R is cycloalkyl, phenyl, phenylalkyl, phenoxy, phenylalkyloxy, phenoxyalkyl, phenylthio, phenylthioalkyl, or cycloalkyl substituted with 1, 2, 3 or 4 halogen groups and/or 1, 2, 3 or 4 lower alkyl groups.

6. An anthelmintic composition comprising an anthelmintic effective amount of a compound as defined in claim 1 and a pharmaceutically acceptable carrier therefor.

7. A method for treating or preventing helminth infestation in mammalian hosts which comprises administering to a mammal an anthelmintic effective amount of an anthelmintic composition as defined in claim 6.

8. The method as defined in claim 7 wherein said composition is administered orally or parenterally.

9. The method as defined in claim 8 wherein said composition is administered parenterally.

* * * * *

UNITED STATES PATENT AND TRADEMARK OFFICE
CERTIFICATE OF CORRECTION

PATENT NO. : 4,293,569

DATED : October 6, 1981

INVENTOR(S) : Rudiger D. Haugwitz et al

It is certified that error appears in the above–identified patent and that said Letters Patent are hereby corrected as shown below:

On the title page, in the title, "PHENYLGUANINDINES" should read --PHENYLGUANIDINES--.
Column 1, line 1, in the title, "PHENYLGUANINDINES" should read --PHENYLGUANIDINES--.
Column 12, Table IV, Column IV, the column heading "$R^{11}$" should read --$R^1$--.

Signed and Sealed this

Ninth Day of March 1982

[SEAL]

Attest:

GERALD J. MOSSINGHOFF

Attesting Officer    Commissioner of Patents and Trademarks